United States Patent [19]

Müller

[11] 4,397,556
[45] Aug. 9, 1983

[54] MATERIAL-TESTING METHOD AND APPARATUS

[75] Inventor: Gerhard Müller, Aalen, Fed. Rep. of Germany

[73] Assignee: Carl Zeiss-Stiftung, Oberkochen, Fed. Rep. of Germany

[21] Appl. No.: 180,407

[22] Filed: Aug. 22, 1980

[30] Foreign Application Priority Data

Sep. 5, 1979 [DE] Fed. Rep. of Germany ....... 2935812

[51] Int. Cl.³ .............................................. G01J 03/44
[52] U.S. Cl. ................................... 356/301; 362/293; 356/417
[58] Field of Search ............... 362/259, 293, 294, 311; 350/163, 168, 311; 356/300, 302, 301; 250/472; 73/104, 105, 432 L

[56] References Cited

U.S. PATENT DOCUMENTS 4,030,827 6/1977 Delhaye et al. ..................... 356/301

OTHER PUBLICATIONS

Heritage, J. P., International Conference on Picosecond Phenomena Springer Series in Chemical Physics, vol. 14, pp. 343-347 (1980).
Silberman et al., Applied Spectroscopy, vol. 32, pp. 352-355 (1978), "High Resolution Interferometric Accessory for Raman Spectrometers".
Schoen et al., Applied Spectroscopy, vol. 33, pp. 178 (1979), "Fabrey-Perot Prefilter for Raman Spectorscopy".
Gardiner, D. J., Analytical Chemistry, vol. 52, pp. 96R-100R (1980), "Raman Spectroscopy".

Primary Examiner—Benjamin R. Padgett
Assistant Examiner—M. Moskowitz
Attorney, Agent, or Firm—Hopgood, Calimafde, Kalil, Blaustein & Judlowe

[57] ABSTRACT

In materials-testing involving comparative examination of the surface of a particular material specimen, specimen surfaces are irradiated with monochromatic light and the Raman spectra of the specimen surfaces are recorded only for certain predetermined spectral regions, the spectral regions having been predetermined through prior recording of the Raman spectra of comparison bodies of different surface character, from which prior recording lines of the spectra which depend on surface character have been selected and classified in accordance with their characteristic properties; characteristic line properties for the specimen recordings are compared to those for the comparison-body recordings in order to make a determination of whether the specimen surfaces are of the acceptable quality represented by the comparison-body surfaces.

15 Claims, 9 Drawing Figures

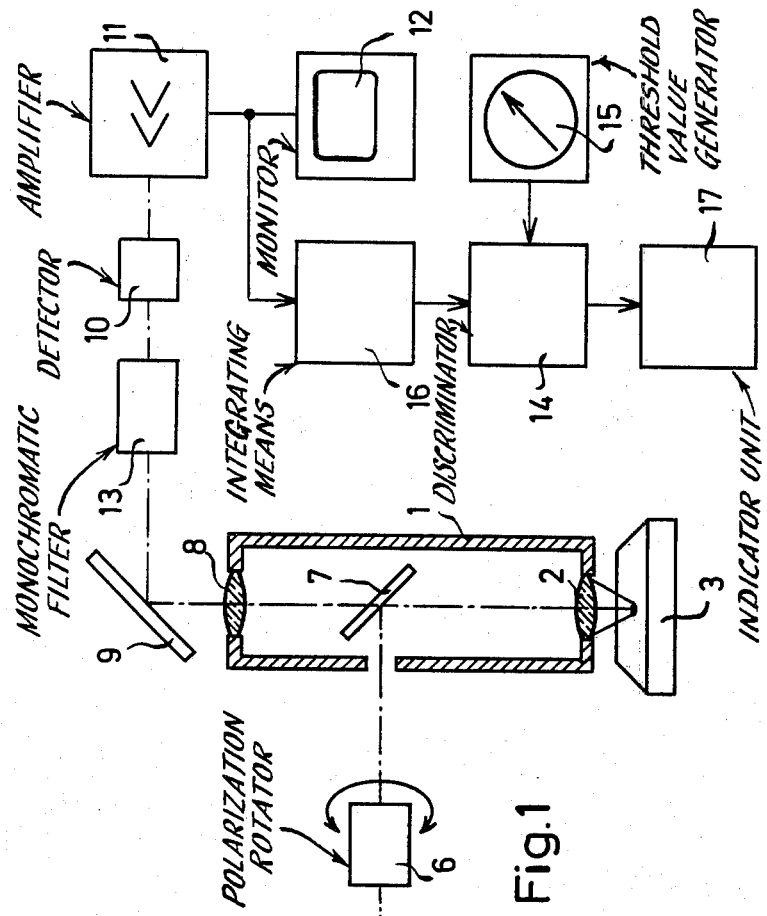
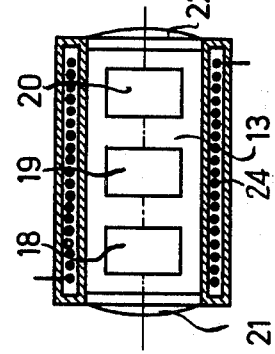

MATERIAL-TESTING METHOD AND APPARATUS

BACKGROUND OF THE INVENTION

This invention relates to a method and apparatus for the testing of material in which the surface of the test piece is irradiated with monochromatic light.

The quality control of surfaces is of fundamental importance, particularly in the field of biomedicine for implant materials, in the field of pharmaceutical production for judging the homogeneity and composition of drugs, in the field of industrial chemistry for the manufacture of catalysts, and in general in the field of material engineering for the production of highly pure, corrosion-resistant materials.

Up to the present time in these fields, quality control, aside from true functional controls of individual specimens, has been effected only by sampling inspections with visual evaluation, with or without microscope, and at times at most by light-spectroscopic individual examination. Such techniques rely essentially on methods which operate with conventional emission or absorption spectroscopy. However, with a reasonable expenditure of personnel and material, such methods yield substantially only overall results which are not very specific; they either involve integration over large regions of the surface, or else their depths of penetration are too great, so that they provide only a mixed signal indicative of surface and interior conditions, or else they are not sufficiently informative with respect to the chemical constitution on a molecular plane, since it is only with difficulty that reflection-spectroscopic examinations in the infrared can be reproduced.

It is, furthermore, already known to study the chemical nature of, for instance, geological specimens by means of Raman spectroscopy. In this case, Raman spectra from different regions of the surface of the specimen are recorded and compared with the spectra of known chemical compounds. From the "Microprobe Mole" brochure published by the Yvon Company, there is known an apparatus with which it is possible not only to record Raman spectra of punctiform regions of microscopic specimens, but the specimen itself can be observed in the light of its characteristic Raman radiation. In this way, the local distribution of the substances to be analyzed can be determined.

The indicated apparatus is an extremely costly and expensive analytical instrument which is not suitable for routine investigation, due to its complicated construction. To observe Raman light on the wavelength characteristic for the specimen and to record the spectra, a special double monochromator is used, permitting continuous scanning over the desired wavelength range. The identification of substances to be analyzed is effected by having the operator compare their spectra with those of known compounds, and this requires a great amount of time.

BRIEF STATEMENT OF THE INVENTION

The object of the present invention is to provide a method and apparatus for the testing of materials by which deviations in the molar structure of surfaces of a test specimen from predetermined desired structures can be recognized rapidly and without any great technical expense.

This object is achieved in a first method of the invention by performing the following operative steps:
  (a) Raman spectra of comparison bodies of different surface character are recorded;
  (b) lines of the spectra which depend on surface character are selected and classified in accordance with their characteristic properties;
  (c) the spectra of the test specimens are recorded in predetermined regions in which the lines dependent on surface character occur; and
  (d) after the extraction of the characteristic line properties, the latter are compared with the desired properties which were previously obtained.

The comparison can be effected by establishing limiting values for the position, width or intensity of characteristic lines, which limiting values will not be exceeded (in the positive or negative direction) by the test piece, these limiting values being derived from the spectra of the comparison bodies. The test, therefore, extends only to a small region of the spectrum of the test piece, i.e., to an interrogation as to the intensity of the Raman radiation at predetermined frequency. A rapid objective testing of the material is thus assured.

In order to obtain, in all cases, unequivocal, reproducible Raman spectra or intensities of individual lines, it is advantageous for purposes of standardization to measure the intensity of the elastically scattered light.

Cases are also known in which the test piece is characterized less by the integral character of its surface than by the spatial distribution, for instance, of its different constituent substances or phases. And to enable meaningful material testing for such cases, the aforementioned objective is realized in a second method of the invention, by performing the following operative steps:
  (a) Raman spectra of comparison bodies of different surface character are recorded;
  (b) lines of spectra which depend on surface character are selected;
  (c) the surface of the specimen is imaged in light of the characteristic part of the spectrum of the test piece; and
  (d) deviation of the spatial distribution of the intensity of the Raman light from predetermined desired structures is used for the verification of the workpiece.

The spatial distribution of the intensity of the Raman light can show, for instance, deviations in shape and size of inclusions, micellestructures, etc., which are not visible under normal microscopic observation but which have a controlling influence in determining the corrosion properties of the test piece. The deviations can be recognized either by an observer who judges the Raman diagram during the examination or afterwards, or else automatically, for instance with means known from television display analysis.

When exposing the specimen for analysis in Raman light, it is advantageous, as aid in orientation, to image the same portion of the surface in elastically scattered (Rayleigh) light.

The methods of the invention are not limited to recognition of contamination of the test piece by substances of different chemical composition. Since the Raman radiation is characteristic of the molecular structure of the objects being examined, changes in the ratio of different modifications of one and the same substance can also be recognized. Different modifications, however, generally also have a different corrosion behavior, so that in this way there is obtained a particularly interesting case of use for material testing.

The recognition of impurities which are bound with different strength to the corresponding test piece, and the subsequent selection of the test piece, are possible since the bonding conditions also affect both the Raman-scattered radiation emitted from the test piece and that emitted by the adsorbents.

The methods of the invention can be advantageously used in biomedicine, for instance for the examination of implants. More specifically, it has been found that the molecular surface structure of solid bodies can be changed by mechanical working, and that these changes manifest themselves in measurable deviations of the Raman spectrum of the worked bodies from that of the unworked bodies. Since the corrosion behavior of practically all materials is strongly dependent on their molecular surface structure, a selection of test pieces based on optimal stability can be effected by means of the invention; such selection is an essential prerequisite, for instance, in the case of implants, since corrosion can produce toxic degradation products in the body.

Further, the methods of the invention can be successfully used in production of pharmaceuticals, in judging the composition and homogeneity of drugs. The first above-noted method is suitable for continuous monitoring of the concentration of one or more components of the agent to be tested, while by means of the second method, as a result of the pictorial representation of the components in their characteristic Raman light, inhomogeneities in their distribution can be recognized.

The invention also provides apparatus for carrying out of the first and second methods. Such apparatus consists of a source of monochromatic light for illuminating the object to be tested, a filter arrangement for suppressing the light used for illumination, an imaging system to produce an image of the test piece in both elastically scattered and Raman-scattered light, and a photoelectric transducer for measuring the intensity of the Raman light. The apparatus is further characterized by the fact that the filter arrangement for the limited-spectrum selection of the Raman light consists of at least two narrow-band filters of fixed characteristic.

Thus, it is not necessary to invest in a costly and expensive frequency-variable double monochromator with high suppression of scattered light; rather, selected filters are used for their specific wavelength passband in the characteristic part of the spectrum of the test piece. Thus-equipped apparatus can therefore be a relatively inexpensive routine device.

Filters of different types can be used, for instance interference filters, Fabry-Perot interferometers, Lyot filters, Christiansen filters, or so-called FTR filters.

Inasmuch as the best filters available at the present time can achieve a suppression of scattered light, in the order of magnitude of between $10^{-3}$ and $10^{-4}$, at least two filters having their passband adapted to each other should be used, to permit detection of the extremely weak Raman radiation.

As a result of their construction, some of these filters have additional passbands (transmission maxima of a different order), i.e., in addition to the passband for which they are designed. Through such filters, undesired scattered radiation reaches the detector so that the latter becomes insensitive for the detection of the characteristic Raman lines. To exclude these higher transmission maxima, it is generally recommended to additionally use colored glasses having wide-band attenuation characteristics.

In using apparatus of the invention, it has been found advisable not to use two identical filters, but rather filters whose characteristics exhibit a somewhat different line width for the characteristic Raman region. In such case, the transmission maxima for other orders of the two filters no longer coincide, since the distance apart of the transmission maxima depends on the width of the characteristic.

By such multiplicative filter action, one obtains not only a further constriction of the desired transmission range, but also an additional extremely effective suppression of scattered light.

It is also possible to combine filters of different type with each other, for instance an interference filter with a Christiansen filter, in order to circumvent the problem of higher transmission maxima.

It is further advantageous to provide a device for controlling the temperature of the filters since the pass characteristics of narrow-band filters are strongly dependent on temperature. This device can be used on the one hand for stabilizing the temperature of the filters (a) to thus maintain the transmission maximum of the filter in the desired wavelength range, for a prolonged period of operation and (b) to be able, by changing the operating temperature, to adapt the filter to the characteristic Raman lines of different test pieces. The filters can therefore be manufactured with large manufacturing tolerances at low cost and be fine-tuned to the particular use requirement by means of a temperature-control unit.

Still further, it has been found advantageous for irradiation of specimens to use a laser whose frequency is continuously variable (for instance, a dye laser). With such a laser, Raman spectra of the test pieces and of the comparison bodies can be recorded by varying the wavelength of the exciting light. If, as is frequently the case, there is no resonance Raman scattering, one obtains the same spectrum as with a variable monochromator and fixed exciter frequency. And the narrow-band filters need not be tuned to the test piece and arranged replaceably for different test pieces; rather, adjustment of the part of the spectrum characteristic to that of the test piece is effected by tuning the wavelength of the laser.

In all the above-mentioned advantageous laser embodiments, a so-called polarization rotator can be arranged between the laser and test piece. Suitable selection of the polarized direction of the exciting light enables an optimizing of the intensity of the Raman radiations. It has further been found advantageous to arrange a line-blocking filter (a so-called Raman notch) for the Raman radiation, such filter being located between test piece and detector; by such means, intensive excitation light on the observation side can be additionally suppressed.

The detector or image-producing means may suitably be a multi-diode target or a television camera tube with image amplifier connected in front of it. The detector or image-producing means may be used, for instance, in combination with a microscope or telescope through which the test piece is observed. With an expansion lens between laser and test piece, the size of the region of the specimen to be illuminated can be selected.

DETAILED DESCRIPTION

Various illustrative examples of the methods and embodiments of the invention will be described in further detail, in conjunction with the accompanying drawings, in which:

FIG. 1 is a block diagram schematically showing the invention in the context of a simple Raman microscope for routine examination;

FIG. 2 is a simplified longitudinal section to show diagrammatically the construction of a monochromatic filter in FIG. 1;

Figure 3A:
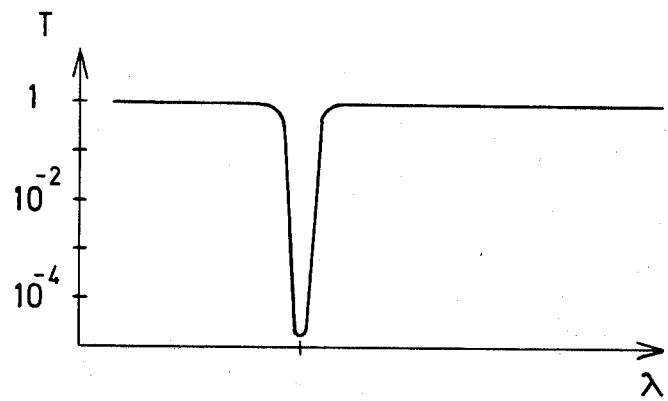
FIGS. 3a and 3b are graphs depicting filter characteristics of three filter component elements in the monochromatic filter of FIG. 2, the graph of FIG. 3a depicting a first filter, the graph of FIG. 3b separately depicting characteristics of the second and third filters, and the graph of FIG. 3c depicting the combined characteristic of the second and third filters.

In FIG. 1, a conventional reflected-light microscope is positioned to observe a test piece 3 under the objective 2.

Excitation light is produced by a laser 4, and after such that has passed through an expansion lens 5, it is fed to a polarization rotator 6 to enable selective change in the direction of polarization.

The microscope 1 includes a beam splitter 7 by which the laser beam is reflected onto the specimen 3. In a variant, it will be understood that the laser light may be focused directly on the specimen.

Raman radiation emitted by the specimen 3 and the very much more intense Rayleigh-scattered radiation pass through beam splitter 7 and are focused by an imaging lens 8 and a mirror 9 upon an image-producing detector 10.

The detector 10 may be, for instance, a television camera tube with image amplifier in front of it, producing a video signal which is amplified at 11 and fed to a monitor 12.

A monochromatic filter 13 in front of the detector 10 is pervious only to the characteristic part of the Raman spectrum of the test piece 3. There is thus displayed at monitor 12 a picture only of the parts of the surface of the test piece 3 which emits this Raman radiation.

At the same time, the video signal, after integration over the entire television picture, is fed to a discriminator 14 in which it is compared with the stored signal of a comparison body which was obtained at the same wavelength. The comparison value, which can be set at a threshold-value generator 15, may consist of an upper or lower limit or of a "window". If the output signal of integrator 16 lies in the signal window of the threshold-value generator 15, then the discriminator 14 reports a positive test result to an indicator unit 17. It will be understood that such a test-result signal may also be used for other purposes; for instance, it may be further processed for automatic sample sorting.

If it is sufficient, for a specific task situation, to determine the light of a Raman band as an integration over a defined surface region, the pictorial display of the test piece in the Raman light can be dispensed with; in such a situation, as a further simplification, a simple photomultiplier may be used as the detector 10, instead of the picture amplifier and associated television camera tube. In this situation, there is no need for the monitor 12 or the integrator 16.

Figure 3B:
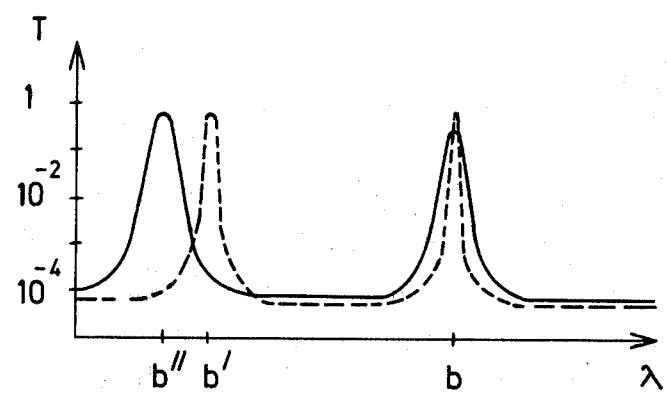

The monochromatic filter 13 used for suppression of scattered light is shown in FIG. 2 to comprise three individual filters 18, 19, 20 arranged one behind the other, and having pass characteristics which are individually shown in FIGS. 3a and 3b. The filters are arranged in the telecentric ray path of an intermediate-imaging, optical system 21-22. The monochromatic filter 13 is surrounded by heating coil means 24 by which temperature stabilization of the monochromatic filter 13 can be obtained via a suitable control unit, not shown.

Figure 3C:
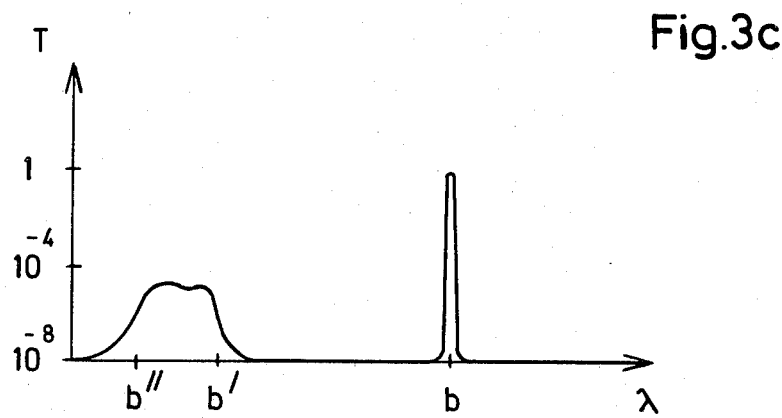

The filter 18 is a line-blocking filter (Raman notch) which is opaque only in a narrow region around the wavelength of the laser 4. It serves to keep the Rayleigh radiation (which is much more intense than the Raman radiation) away from the detector during the actual measurement. The filters 19 and 20 may be interference filters which are transparent to a wavelength b which is characteristic of the test piece. Their pass characteristics (FIG. 3b) show that the respective filters 19 and 20 have further transmission maxima of different order (b', b"). If the filters 19 and 20 are made identical, then the other-order transmission maxima of the two filters coincide substantially, and no substantial scattered-light suppression can be obtained in these regions. Preferably, the filters 19 and 20 are so selected that their transmission maxima lie at the same wavelength b but the width of the transmission lines is different. Since there is a fixed relationship between the distance apart of the transmission maxima and the width of the lines, the other-order maxima of filters 19 and 20 do not coincide; and FIG. 3c shows that the overall characteristic which results from multiplication of the individual characteristics of filters 19 and 20 enables significant suppression of scattered light within the entire wavelength range for which the detector 10 is sensitive. Further suppression of undesired wavelengths can be obtained with use of additional color filters customarily used with interference filters.

Figure 4A:
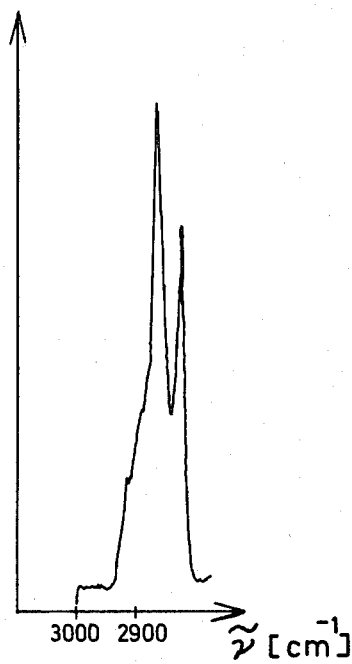
FIGS. 4a and 4b are graphs depicting the Raman spectra of two test pieces, of slightly different surface character.
Figure 4B:
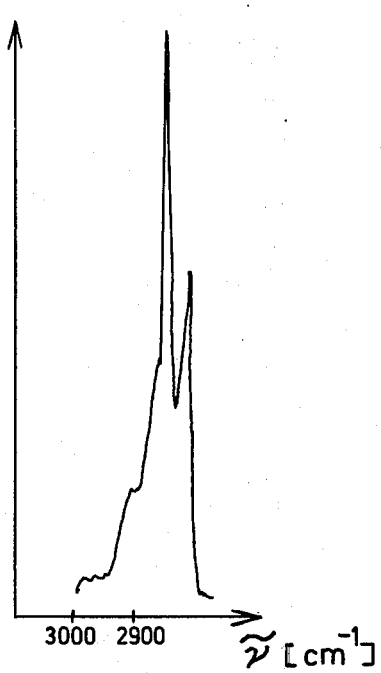

FIG. 4 diagrams show a part of the Raman spectrum of polyethylene before (FIG. 4a) and after (FIG. 4b) mechanical surface working. The spectra differ in the intensity ratio of the Raman lines produced by the symmetrical and asymmetrical $CH_2$ stretch vibrations. The effect is based on a change in the micellestructure of the polyethylene surface, by reason of mechanical working. Since the stability of implants and also the toxicity of implant materials, which include polyethylene, depend on the surface structure of the implants, it is desirable to examine the same before implantation and to sort out test pieces of strongly disoriented surface structure.

By the method of the invention, it is possible to effect an automatic verification process in which the intensity of one of the two lines of the $CH_2$ stretch vibration of the test piece consisting of polyethylene is compared with desired intensities which have been determined from a comparison spectrum.

Another example of use is the checking of catalysts in industrial chemistry, both upon their manufacture and also at certain time intervals during their use.

There are many cases in which it is not the integral quantity of the surface changes but rather their shape which is characteristic of the test piece. Thus it can be significant, for instance, to determine the size of inclusions in solids or of particles in liquids which do not stand out from the surrounding medium, either in their index of refraction or in their absorption properties.

Figure 5A:
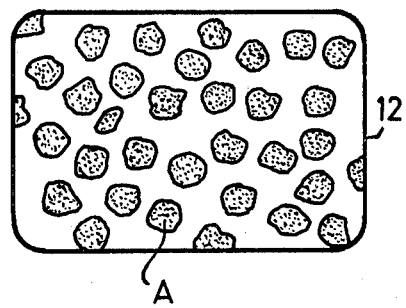
FIGS. 5a and 5b are diagrammatic presentations of the images of two test pieces of different surface structure, recorded in the light of their characteristic Raman bands.
Figure 5B:
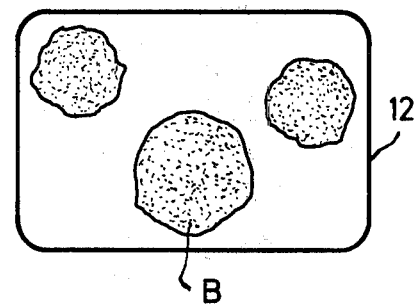

If a monochromatic filter 13 tuned to the characteristic Raman lines of these inclusions is used, one then obtains diagrams as sketched in FIGS. 5a and 5b for two test pieces with different-size inclusions. The size of the inclusions A and B can be determined by means of devices known from television-display analysis and can be compared with desired sizes. A distinguishing of the test pieces whose Raman pictures are shown in FIGS. 5a and 5b is therefore possible even if the substance present in both test pieces is present in the same concentration in the test piece; such problems arise in particular in the field of pharmaceutical production, for instance upon the verification of the homogeneity of drugs.

I claim:

1. The method of testing a test piece of a given material, wherein the test piece is irradiated with monochromatic light and resulting Raman-scattered radiation is detected in a spectral region that has been selected by prior such observation of reference pieces, and further wherein:
   (a) the measured value of the Raman radiation of the reference pieces in at least one spectral region is used to establish a trigger-threshold signal,
   (b) comparing, against said trigger-threshold signal and by electronic discrimination, the signal indicative of Raman intensity for the test piece in said spectral region, and
   (c) using the output signal of the discriminator to classify the test pieces.

2. A method according to claim 1, characterized by the fact that the intensity of the elastically scattered light is furthermore measured for the standardizing of the spectra.

3. A method according to claim 1, characterized by its use for quality control in the field of biomedicine.

4. A method according to claim 1, characterized by the fact that implant materials are examined.

5. A method according to claim 1, characterized by the fact that it is used in industrial chemistry in particular for the testing of catalysts.

6. A method according to claim 1, characterized by the fact that it is used in pharmaceutical production in order to judge the homogeneity and composition of drugs.

7. Apparatus for carrying out the method of claim 1, comprising a source of monochromatic light for illuminating the test piece, an imaging system for producing an image of the test piece in elastically scattered light and in Raman light, a photoelectric transducer for measuring the intensity of the Raman light, filter means for suppressing transducer response to the light used for illumination, said filter means consisting of at least two narrow-band filters of fixed characteristic, a signal generator providing a selectable trigger-threshold signal, and a discriminator connected for comparative response to the output of said transducer and of said signal generator.

8. An apparatus according to claim 7, characterized by the fact that the source of monochromatic light consists of a variable-frequency laser.

9. An apparatus according to claim 8, characterized by the fact that with fixed laser frequency, the filters are so selected that their passband falls within the characteristic part of the Raman spectrum of the test piece.

10. An apparatus according to claim 7, characterized by the fact that interference, FTR, Christiansen, Lyot or Fabry-Perot filters are used.

11. An apparatus according to claim 7, characterized by the fact that the filter arrangement consists of a combination of different types of filters.

12. An apparatus according to claim 7, characterized by the fact that the filter arrangement contains at least two interference filters of different characteristics whose transmission maxima agree only for one wavelength.

13. An apparatus according to claim 7, characterized by means for varying the temperature of the filters.

14. An apparatus according to claim 7, characterized by the fact that a polarization rotator is arranged between the source of monochromatic light and the test piece.

15. An apparatus according to claim 7, characterized by the fact that in order to examine a larger section of the surface of the specimen an expansion lens is placed behind the laser.

* * * * *